United States Patent [19]

Milner et al.

[11] 4,332,962

[45] Jun. 1, 1982

[54] PREPARATION OF CYCLOPROPANE CARBOXYLIC ACID ESTERS

[75] Inventors: David J. Milner; David Holland, both of Runcorn, England

[73] Assignee: Imperial Chemical Industries Limited, London, England

[21] Appl. No.: 238,950

[22] Filed: Feb. 27, 1981

Related U.S. Application Data

[63] Continuation of Ser. No. 49,322, Jun. 18, 1979, abandoned, which is a continuation of Ser. No. 883,310, Mar. 3, 1978, abandoned.

[30] Foreign Application Priority Data

Mar. 11, 1977 [GB] United Kingdom ............... 10401/77

[51] Int. Cl.$^3$ ................... C07D 307/45; C07C 69/743
[52] U.S. Cl. ............................. 560/124; 252/431 C; 549/499
[58] Field of Search ...................... 560/124; 260/347.4

[56] References Cited

U.S. PATENT DOCUMENTS 3,808,260  4/1974  Yoshikawa ........................ 560/124
3,868,401  2/1975  Aratani ............................... 560/124
3,897,148  7/1975  Shim .................................. 560/124
4,024,163  5/1977  Elliott ................................ 560/124

FOREIGN PATENT DOCUMENTS 2554380  6/1976  Fed. Rep. of Germany ...... 560/124
51-4150  1/1976  Japan ................................. 562/506

OTHER PUBLICATIONS

Legzdins, J. Chem. Soc., (A), pp. 3322–3326 (1970).
Hubart, Synthesis, (9), pp. 600–602 (1976).

*Primary Examiner*—Michael L. Shippen
*Attorney, Agent, or Firm*—Cushman, Darby & Cushman

[57] ABSTRACT

Process for the preparation of 3(2,2-dihalovinyl)-2,2-dimethyl cyclopropane carboxylic acids, especially permethrin acid ethyl ester, by reacting a diazoacetic acid ester with a 1,1-dihalo-4-methyl-1,3-pentadiene in the presence of a catalyst comprising a divalent rhodium salt of a carboxylic acid or borofluoric acid. The products have improved yields and better cis/trans isomer ratios than when the more common catalysts, e.g. copper-bronze, are used.

6 Claims, No Drawings

PREPARATION OF CYCLOPROPANE CARBOXYLIC ACID ESTERS

This is a continuation of application Ser. No. 49,322, filed June 18, 1979, now abandoned, which is a continuation of Ser. No. 883,310, filed Mar. 3, 1978, now abandoned.

This invention relates to the preparation of cyclopropane carboxylic acid esters from alkenes and, especially, halogenated dienes, to form compounds useful as insecticides or insecticide intermediates. More particularly it relates to the preparation of esters of 3(2,2-dichlorovinyl)-2,2-dimethylcyclopropane carboxylic acid, for example the ethyl ester, commonly referred to as permethrin acid ethyl ester (PAE).

PAE exists in four isomeric forms, that is, cis and trans, each of which may be in the 1S or 1R optically active form. When PAE is used as an insecticide intermediate, both 1S isomers are totally inactive and of the 1R isomers the cis form is approximately twice as active as the trans. Since the thermodynamic equilibrium mixture contains about 20% cis and about 80% trans isomers (the proportion of S and R forms being equal), it is highly desirable to increase the proportion of cis isomers in the product.

PAE may be prepared by the reaction of 1,1-dihalo-4-methyl-1,3-pentadiene with an ester of diazoacetic acid, as described by Farkas et al (Coll. Czech Chem. Comm, 1959, 24 pp 2230–2236) and when this reaction is catalysed by the catalysts commonly used, e.g. copper bronze, the product contains a predominance of the trans isomer. On the other hand, when the reaction is catalysed by palladium acetate a predominance of the cis isomer is produced; however, the total yield of product is unacceptably reduced.

We have now found that by catalysing the reaction with certain rhodium salts one may obtain a good overall yield of products having satisfactory cis/trans ratios.

According to the present invention, a process for the preparation of an ester of 3(2,2-dihalovinyl)-2,2-dimethylcyclo-propane carboxylic acid comprises reacting a 1,1-dihalo-4-methyl-1,3-pentadiene with an ester of diazoacetic acid in the presence of a divalent rhodium salt of a carboxylic acid or borofluoric acid, as catalyst.

By "dihalo" we mean dichloro, dibromo or chlorobromo.

The reaction is preferably carried out in the presence of an inert solvent in which the product is soluble.

Conveniently the solvent used is immiscible with water to facilitate preparation of the diazoacetic ester. More preferably the solvent also has a boiling point lower than that of the 1,1-dihalo-4-methyl-1,3-pentadiene to facilitate recovery of unreacted diene.

Suitable solvents include saturated chlorinated hydrocarbon solvents, such as ethylene dichloride, dichloromethane, tetrachloroethane, carbon tetrachloride and the like.

A wide variety of divalent rhodium salts of carboxylic acids may be used as catalyst, the precise cis/trans ratio of the product being dependent, inter alia, upon the actual salt used. Suitable divalent rhodium salts, apart from the borofluoride, include the pivalate, octoate, benzoate, p-chlorobenzoate, p-methoxy benzoate, m-methoxybenzoate, triphenyl acetate and acetyl mandelate. The acetate may also be used; but it tends to give lower yields than some of the other salts referred to above.

It is noted that neither monovalent nor trivalent rhodium salts give rise to the desired effect.

The concentration of catalyst in the reaction mixture is not critical, but generally concentrations in the range of 0.00001 to 1 g atoms of Rh(II) per liter of reaction mixture, and especially 0.005 to 1 g atoms, are suitable.

The temperature of reaction is generally in the range $-10°$ to $+130°$ C., preferably $10°$ to $90°$ C. It will be noted that these temperature ranges are lower than those usually required when other commonly used catalysts e.g. copper-bronze are employed. In fact, the reaction may be initiated without external heating, which is not possible with, say, copper-bronze catalysts.

The diazoacetic acid ester may be prepared by reacting a water soluble acid addition salt (e.g. the hydrochloride) of an ester of glycine with an alkali metal nitrite in an aqueous medium, which is stirred with a water-immiscible solvent into which the diazoacetic acid ester is dissolved. Alkali metal nitrites which may be used are, for example, the potassium or sodium salts, and the reaction with the glycine ester is preferably carried out in the presence of an acid catalyst, for example, sulphuric acid.

The solution of diazoacetic acid ester thus formed is then added to a solution of the 1,1-dihalo-4-methyl-1,3-pentadiene maintained at the desired temperature, and containing the divalent rhodium salt catalyst, usually in solution.

It is usual to use excess diene, the ratio of diene to diazoacetic ester being in the range 2/1 to 10/1.

Progress of the reaction may be monitored by measuring nitrogen evolution, which may also be used to determine yield of total products, the proportion of the desired product being readily determined by gas liquid chromatography (glc).

Separation of the desired product from the reaction mixture may be achieved by any convenient means; but it is generally convenient to first distil off the solvent, the diene, then any esters of maleic and fumaric acids and finally the required product. Alternatively, the crude product, after removal of solvent and unreacted diene, may be used as an intermediate without further purification. This latter procedure is particularly appropriate when using the process of the present invention, since many of our rhodium catalysts give rise to high efficiency in the use of the diazoacetic acid ester, with a consequently lower proportion of by-products (e.g. esters of maleic and fumaric acid) than are formed using the more usual catalysts.

As has previously been mentioned one would ideally desire to increase not only the cis/trans ratio of the product, but also the proportion of the insecticidally active optical isomer. This may be achieved by using a catalyst comprising a rhodium salt of an appropriate optical isomer of an optically active carboxylic acid, e.g. of acetyl mandelic acid. It may sometimes be difficult to predict which optical isomer of a particular carboxylic acid will give an enhanced proportion of the desired optical isomer of the product; but this may be readily determined experimentally by testing each optical isomer in turn and determining the product distribution e.g. by glc analysis.

The reaction may also be performed continuously by forming the diazoacetic ester in a first vessel and continuously transferring it, in a solvent, to a second vessel where it is reacted immediately with the diene, as described and claimed in our British Pat. No. 1,459,285.

Our process may be used to produce a variety of esters of the 3(2,2-dichlorovinyl)-2,2-dimethylcyclopropane carboxylic acid, the particular ester produced being dependent upon the particular glycine ester used. Thus the process may be used to produce simple alkyl esters, which are useful as intermediates in the preparation of insecticides, or it may be used to produce the insecticides themselves. In the latter case the glycine ester must correspond to the required insecticidal ester. Examples of glycine esters of this type include the ester with 3-phenoxybenzyl alcohol, and with 5-benzyl-3-furyl methanol.

The invention will now be illustrated by the following Examples.

carboxylates gave very low yields and, with the exception of palladium acetate, poor cis/trans ratios. Monovalent and trivalent rhodium salt catalysts were also unsatisfactory. When $Rh(II)$ $Cl_2[(O-tolyl)_3P]_2$ was used as catalyst, that is a divalent rhodium compound other than a carboxylate or borofluoride, at 60° C., the evolution of nitrogen was fairly rapid; but the yield of PAE was only 1.3%.

TABLE I

| Ex No | Divalent Rhodium Compound Catalyst | Reaction Time (min) | Temp (°C.) | Rate of DAE Add$^n$. (m . mol/min) | Total Yield of PAE (%) | Isomer Ratio % Cis | Isomer Ratio % Trans |
|---|---|---|---|---|---|---|---|
| 1 | Pivalate | 120 | 20 | 0.016 | 53 | 58 | 42 |
| 2 | Octoate | 180 | 20 | 0.014 | 62 | 54 | 46 |
| 3 | Benzoate | 120 | 20 | 0.013 | 48 | 58 | 42 |
| 4 | Diphenylacetate | 120 | 20 | 0.012 | 50 | 49 | 51 |
| 5 | Triphenylacetate | 30 | 80 | 0.016 | 90 | 59 | 41 |
| 6 | Acetylmandelate | 300 | 80 | 0.019 | 30 | 48 | 52 |
| 7 | p-Methoxybenzoate | 30 | 20 | 0.011 | 99 | 60 | 40 |
| 8 | p-Chlorobenzoate | 120 | 20 | 0.014 | 46 | 62 | 38 |
| 9 | Chloroacetate | 120 | 20 | 0.013 | 29 | 49 | 51 |
| 10 | Borofluoride | 155 | 20 | 0.013 | 66 | 53 | 47 |
| 11 | Acetate | 120 | 20 | 0.015 | 18 | 50 | 50 |
| 12 | m-Methoxybenzoate | 180 | 20 | 0.011 | 51 | 61 | 39 |
| 13 | α-D-methyl camphorate | 105 | 20 | 0.019 | 27 | 58 | 42 |
| CT* | Cu Bronze | 105 | 80 | 0.014 | 25 | 41 | 59 |
| CT | Mn(II)Naphthenate | 120 | 84 | 0.013 | 8 | 38 | 62 |
| CT | Fe(II)Naphthenate | 180 | 84 | 0.015 | 8 | 38 | 62 |
| CT | Pd(II)Acetate | 120 | 80 | 0.012 | 2.5 | 72 | 28 |
| CT | Rh(III)Chloride | 120 | 83 | 0.012 | 4.1 | 36 | 64 |
| CT | $[(C_2H_4)_2RhCl]_2$ | 90 | 83 | 0.018 | Nil | — | — |

*CT = Comparative test

EXAMPLES 1–14

General Procedure

DCMP-1,3 (1,1 dichloro-4-methyl-1,3-pentadiene) (1.81 g, 12 m.mole)) was added to a measured quantity of the appropriate catalyst (≡0.01 mg atoms of metal) under an atmosphere of nitrogen. A solution (0.25 ml) containing dodecane (1.76 m.mole per ml) in a chlorinated solvent (1,2 dichloroethane or 1,1,2,2 tetrachloroethane) was added as a glc internal standard. The mixture was then heated to reaction temperature, with stirring, under an atmosphere of nitrogen. A solution containing DCMP-1,3 (12 m.mole) and DAE (diazoacetic acid ethyl ester) (3 m.mole) in a chlorinated solvent (2 ml) was then added to the stirred mixture over a period of 4 hours. Nitrogen evolution was monitored throughout the reaction and small samples of the reaction mixture were withdrawn from time to time for glc analysis. Glc product analysis was carried out using a 5 ft, 3% silicone O.V.17 on acid washed chromasorb column maintained at 130° C. The geometric isomer ratio was determined using a 9 ft, 3% silicone O.V.17 column at 127° C.

% yields were determined in terms of moles of PAE per mole of nitrogen evolved (i.e. mole of diazoacetic ester decomposed). Results are set out in Table 1.

It will be seen from these, that a wide variety of divalent rhodium carboxylates and divalent rhodium borofluoride gave good yields of PAE, with enhanced cis/trans ratios. In contrast to this, when the commonly used copper bronze was employed, the total yield was lower and cis/trans ratio less acceptable. Other metal

EXAMPLE 15

The general procedure of Examples 1–14 was followed, using rhodium(II) D(−) acetylmandelate as catalyst. The reaction between DAE and DCMP-1,3 went smoothly at 80° C. giving a 30% yield of PAE based on DAE consumed. The cis/trans ratio of the PAE produced was 48/52.

The solvent for the reaction (1,2-dichloroethane) was removed using a rotary evaporator and the PAE isolated by column chromatography using an alumina (type H) column. Unreacted DCMP-1,3 was washed from the column by elution with petroleum ether (40°–60° C.) and the PAE subsequently recovered by elution with diethyl ether. Diethyl fumarate and diethyl maleate co-products remained on the column.

The PAE was hydrolysed with ethanolic NaOH to give the free acid which was treated with thionyl chloride to give the acid chloride. This was reacted with 2-D-octanol to give a mixture of four isomers. These were analysed by glc on a 15 ft column of 5% LAC-2R-446 on Embacel at 125° C. Of the two diastereoisomers derived from the cis PAE, there was found to be an excess of the 2-D-octyl ester having the longer retention time. The enantiomeric excess was 4.0%

EXAMPLE 16

The procedure of Example 15 was repeated using rhodium(II)L(+) acetylmandelate there was an excess of the 2-D-octyl ester having the shorter retention time. These last two Examples demonstrate that some enhancement of the proportion of one or other optical isomer of PAE is possible using the appropriate catalyst compound.

EXAMPLE 17

A solution of DAE (30 m.mole) in 1,2-dichloroethane was added to a stirred mixture of 1,1′dibromo-4-methyl-penta-1,3-diene (28 m.mole) and a weight of catalyst equivalent to 0.014 mg atoms of metal. The rate of addition was maintained at 0.023 m.mole/min. and reaction was carried out under an atmosphere of nitrogen at the temperature stated. The products were analysed by glc (using a 15 ft LAC2R446 column at 110° C.); and by NMR on a sample isolated by column chromatography (using a neutral alumina column eluted with petrol, diethyl ether). The cis/trans ratios obtained were the same by each technique. Results are given in Table 2. CT is a comparative test.

TABLE 2

|  | Catalyst | Temp (°C.) | Isomer Ratio % Cis | Isomer Ratio % Trans |
|---|---|---|---|---|
| Ex. 17 | Rh(II) Pivalate | 50 | 70 | 30 |
| CT | Cu Bronze | 84 | 27 | 73 |

EXAMPLE 18

DCMP-1,3 (28 m.mole) was added to the catalyst under nitrogen. A solution (0.25 ml) containing dodecane (1.76 m.mole per ml) dissolved in dichloroethane was added as an internal glc standard. The mixture was brought to reaction temperature, with continuous stirring maintained under an atmosphere of nitrogen. A solution of DAE (30 m.mole) in dichloroethane (30 ml) was then added to the mixture over a period of 23 hours. Nitrogen evolution was monitored and small samples of the reaction mixture were withdrawn periodically for glc analysis. The results are given in Table 3. It will be seen that the divalent rhodium pivalate catalyst was as effective as the copper containing catalyst with regard to effective use of DCMP-1,3; but was much more efficient with regard to utilisation of DAE and gave a greatly enhanced cis/trans ratio.

TABLE 3

|  | Catalyst (m. mole) | Temp °C. | Products (m. mole) PAE | Products (m. mole) $N_2$ | DCMP-1,3 Unreacted (m. mole) | Conversion DAE to PAE (%) | Yield* PAE(%) A | Yield* PAE(%) B | Cis/Trans Ratio |
|---|---|---|---|---|---|---|---|---|---|
| Ex 18 | Rh(II) Pivalate (0.005) | 20 | 19.1 | 28.8 | 2.7 | 64 | 76 | 66 | 60/40 |
| CT | $CuSO_4$ $5H_2O$ (0.06) | 80 | 14.0 | 30.0 | 9.3 | 47 | 77 | 48 | 44/56 |
| CT | None | 64 | 0.7 | 4.5 | not measured | 2.3 | — | 15 | 44/56 |

*A - calculated on DCMP-1,3 consumed
B - calculated on $N_2$ evolved.

We claim:

1. A process for the preparation of an ester of 3(2,2-dihalovinyl)-2,2-dimethylcyclo-propane carboxylic acid, said process comprising reacting a 1,1-dihalo-4-methyl-1,3-pentadiene with an alkyl ester or ester of 3-phenoxyl benzyl alcohol or 5-benzyl-3-furyl methanol of diazoacetic acid in the presence of a divalent rhodium salt which is a pivalate, octoate, benzoate, triphenyl acetate, acetylmandelate, p-methoxybenzoate, p-chlorobenzoate, acetate, n-methoxybenzoate, α-D-methyl camphorate or borofluoride, as a catalyst.

2. A process as claimed in claim 1 in which the reaction is carried out in the presence of an inert solvent in which the product is soluble.

3. A process as claimed in claim 2 in which the solvent is a saturated chlorinated hydrocarbon.

4. A process as claimed in claim 1 in which the reaction temperature is in the range 10° to 90° C.

5. A process as claimed in claim 1 in which the concentration of divalent rhodium salt is in the range 0.005 to 1 g atoms of rhodium per liter of reaction mixture.

6. A process for the preparation of permethrin acid ethyl ester with an increased cis/trans ratio which comprises reacting 1,1-dichloro-4-methyl-1,3- pentadiene with diazoacetic acid ethyl ester in the presence of a divalent rhodium walt which is a pivalate, octoate, benzoate, triphenyl acetate, p-methoxybenzoate, p-chlorobenzoate, acetate, m-methoxybenzoate, α-D-methyl camphorate or borofluoride, as catalyst.

* * * * *